(12) United States Patent
Travis et al.

(10) Patent No.: US 12,653,978 B2
(45) Date of Patent: Jun. 16, 2026

(54) ADJUSTABLE NASOPHARYNGEAL AIRWAY DEVICE AND METHOD

(71) Applicant: Code 1 Medical Devices, LLC, St. Petersburg, FL (US)

(72) Inventors: Nicholas Travis, St. Petersburg, FL (US); Brian Travis, St. Petersburg, FL (US)

(73) Assignee: Code 1 Medical Devices, LLC, Seminole, FL (US)

( * ) Notice: Subject to any disclaimer, the term of this patent is extended or adjusted under 35 U.S.C. 154(b) by 0 days.

(21) Appl. No.: 19/120,668

(22) Filed: Apr. 11, 2025

(65) Prior Publication Data

US 2025/0269130 A1 Aug. 28, 2025

Related U.S. Application Data

(63) Continuation of application No. PCT/US2023/035000, filed on Oct. 12, 2023.

(60) Provisional application No. 63/415,634, filed on Oct. 12, 2022.

(51) Int. Cl.
A61M 16/04 (2006.01)
A61M 16/06 (2006.01)

(52) U.S. Cl.
CPC .... A61M 16/0461 (2013.01); A61M 16/0666 (2013.01); A61M 2205/0216 (2013.01); A61M 2209/06 (2013.01)

(58) Field of Classification Search
CPC ............ A61M 16/0409; A61M 16/044; A61M 16/0445; A61M 16/0461; A61M 16/0463;
A61M 16/0484; A61M 16/0486; A61M 16/0488; A61M 2025/0081; A61M 2205/0216; A61M 2205/0266; A61M 2205/36; A61M 2205/587; A61M 2207/00; A61M 2210/005; A61M 2210/0618;

(Continued)

(56) References Cited

U.S. PATENT DOCUMENTS 4,056,104 A * 11/1977 Jaffe ...................... A61M 16/04
128/207.15
4,530,354 A * 7/1985 Froilan ................. A61M 25/02
128/207.17

(Continued)

FOREIGN PATENT DOCUMENTS

CN 216934346 U 7/2022

*Primary Examiner* — Annette Dixon
(74) *Attorney, Agent, or Firm* — Paradies Law P.A.

(57) ABSTRACT

A nasopharyngeal device comprises an adjustment mechanism comprising a bolster on a first portion, tubular airway portion extending away from the bolster wherein a continuous airway is provided through an entire length of the airway defined through the bolster and the tubular airway portion, and the tubular airway portion extends froth a proximal end adjustably coupled with the first portion of the adjustment mechanism to a distal tip of the tubular airway portion, wherein the first portion is adjustably coupled to the proximal end of the tubular airway portion such that the first portion slidingly adjusts a length of the first portion within the proximal end of the tubular airway portion such that a distance between the bolster and the distal tip is selectively adjusted to a specific nare to epiglottis distance.

15 Claims, 14 Drawing Sheets

(58) Field of Classification Search
    CPC .... A61M 2210/0625; A61M 2230/005; A61M
                25/0068; A61M 25/0074; A61M 25/01
    See application file for complete search history.

(56) References Cited

U.S. PATENT DOCUMENTS

| | | | | |
|---|---|---|---|---|
| 4,763,667 | A * | 8/1988 | Manzo | A61M 25/01 |
| | | | | 604/173 |
| 5,507,279 | A * | 4/1996 | Fortune | A61M 16/0472 |
| | | | | 128/207.29 |
| 5,606,966 | A * | 3/1997 | Smith | B01D 39/1623 |
| | | | | 128/200.26 |
| 5,692,506 | A * | 12/1997 | Linder | A61M 25/0068 |
| | | | | 607/124 |
| 6,055,984 | A * | 5/2000 | Brain | A61M 16/0431 |
| | | | | 128/207.14 |
| 6,394,093 | B1 | 5/2002 | Lethi | |
| 2005/0081860 | A1 * | 4/2005 | Gonzales | A61M 16/0465 |
| | | | | 128/207.14 |
| 2006/0266366 | A1 * | 11/2006 | Tsukashima | A61M 16/0488 |
| | | | | 128/207.14 |
| 2007/0227543 | A1 * | 10/2007 | Peichel | A61M 25/00 |
| | | | | 128/207.14 |
| 2010/0300450 | A1 | 12/2010 | Barodka | |
| 2017/0157369 | A1 * | 6/2017 | Faith | A61M 25/10181 |
| 2022/0218930 | A1 | 7/2022 | Trivedi | |

* cited by examiner

FIG. 1
FIG. 2
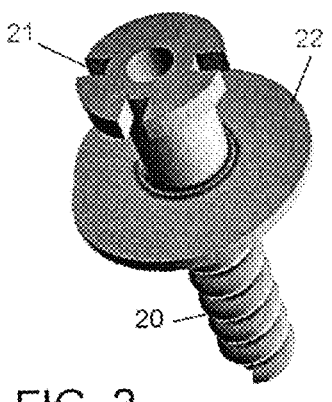
FIG. 4
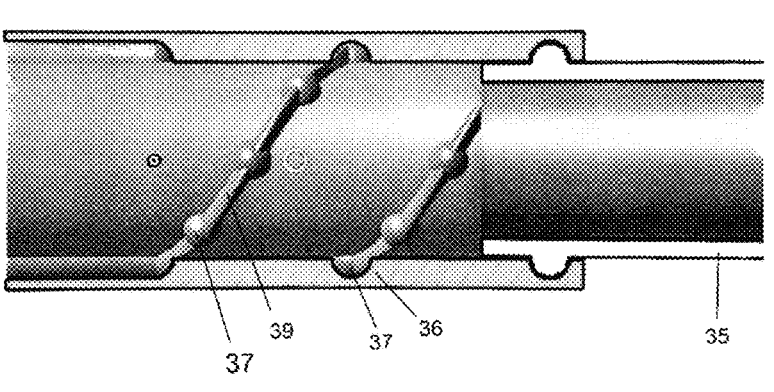
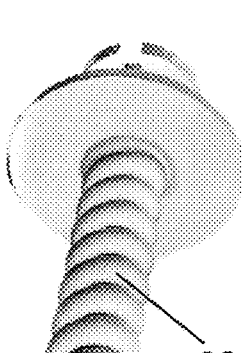
FIG. 3

FIG. 5
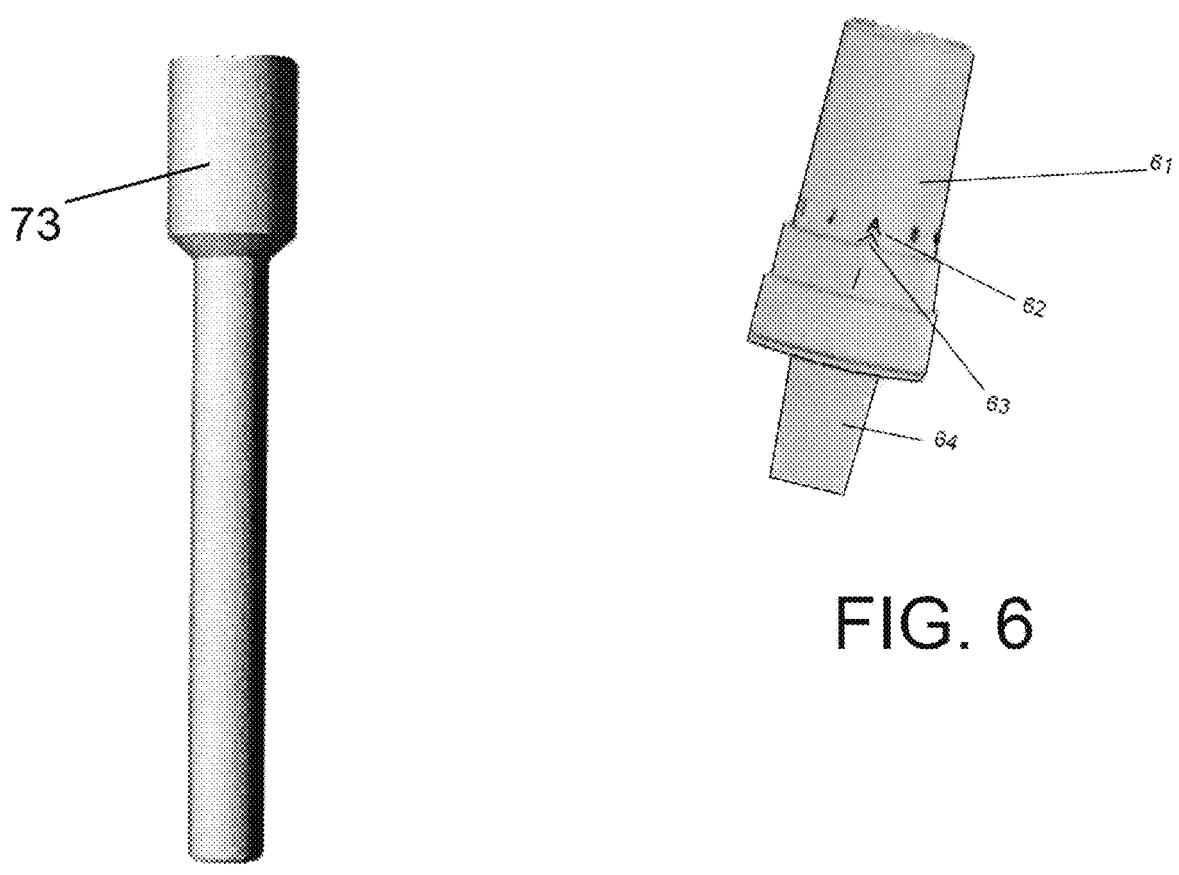
FIG. 6
FIG. 7
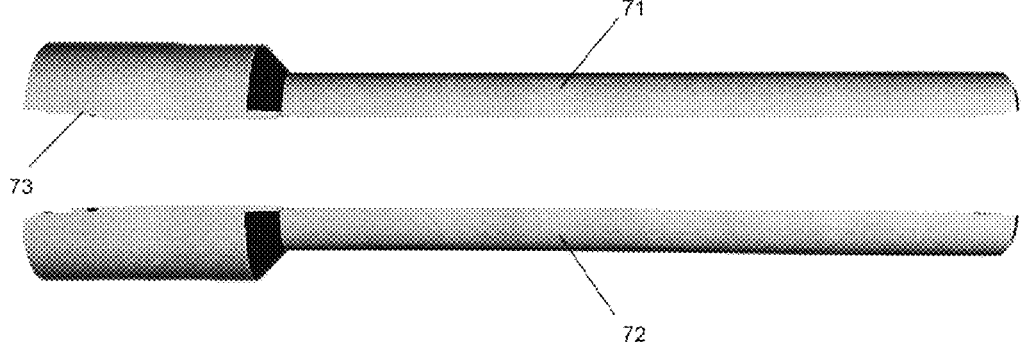

81    82    83

73

B

C

A

15

15

15

ADJUSTABLE NASOPHARYNGEAL AIRWAY DEVICE AND METHOD

CROSS RELATED APPLICATION

This application is continuation application which claims priority to PCT/US2023/035000 filed Oct. 12, 2022, which claims priority to U.S. provisional 63/415,634 which was filed Oct. 12, 2022, which is incorporated by reference herein in its entirety.

FIELD OF THE INVENTION

The field relates to nasopharyngeal devices.

BACKGROUND

A nasopharyngeal airway (NPA) is used in airway management for delivering air and/or oxygen in emergency healthcare situations, both prehospital and in emergencies and surgical suites in hospitals. In order to be used, practically, NPAs should be easy to use, lightweight, and cost-effective. NPAs are inserted into the nasopharynx of a patient. The distal tip of NPAs enters first lifts the base of the tongue from the pharyngeal wall, resolving upper airway obstructions caused by the tongue. In contrast, oropharyngeal airway devices are orally inserted, may be more easily dislodged and may be more likely to cause gagging if the patient is conscious or semiconscious.

Known NPAs have a length that may or may not lend itself to positioning at the proper location. Optimally, an NPA should go deep enough to open the airway while not extending so far into the airway that the device triggers gagging or coughing. In some examples, choosing the wrong length can cause obstruction of the larynx. Operative placement extends the distal tip at a specific location such that the base of the tongue is removed from pharyngeal wall, opening the airway, but prevents the distal tip from proceeding any further. In practice, a bolster or flange is fixed to NPAs that prevents the distal end, or even the entire tube, from proceeding further into the airway, by abutting the bolster or flange to the exterior surface of a patient's nose.

If the NPA is too short, the distal tip fails to reach the base of the tongue and is inoperative for its intended purpose. If the NPA is too long, the distal tip extends too far, which can cause complications, such as gastric distention and aspiration if positioned too far along the esophagus or gagging, vomiting, aspiration, or airway obstruction if positioned too far toward the larynx.

Operatively an NPA should be placed 10 millimeters above the patient's epiglottis, but this location varies from patient to patient. Various ways of estimating the length are known, based on the height of a patient or the like. However, procedures for estimating the length of a tube may require trial and error in an emergency situation. Various lengths of fixed length tubes may be provided, requiring the insertion and removal of one or more tubes if the correct length is not immediately selected. There are possible complications with insertion of NPAs, such as abrasions of the airway and the like, which increase in frequency with multiple insertions of differently sized NPAs, and due to the emergency situation, an improperly sized NPA may be used, operatively for a time, by not fully inserting an NPA that is longer than it should be. This may require use of tape or other work around to prevent said complications but introduces additional risks to the patient.

Therefore, emergency and hospital personnel use common techniques in an effort to properly size NPAs on the first try. The most common method is to measure the distance between the nose tip and earlobe. Alternatively, a user may compare the NPA tube diameter to a patient's nostril size or size of the patient's little finger. Unfortunately, research suggests that these methods are flawed. Other than MRI imaging of the airway, the most effective metric for estimate of NPA length is a patient's height, but this may be difficult to measure in an emergency situation. Two equations are recognized herein: Nare to epiglottis distance in millimeters equals −5.38+0.915× patient height in centimeters, and Nare-Epiglottis Distance equals 4.054+0.067× patient height in centimeters. These equations calculate the optimal NPA length for patients based on their height in centimeters. Even a few inches of height difference may require a different NPA tube length for operative placement of the tube with the bolster/flange securely positioned at the external surface of a nare.

SUMMARY

A nasopharyngeal device comprises an adjustable length between a nare flange that prevent the device from proceeding further into the airway and a distal tip for entry through the nasopharyngeal airway to an operative position that lifts the base of the tongue from the pharyngeal wall without causing other complications. For example, a corkscrew shaped member may be matingly inserted within an extending member such that rotation of the corkscrew shaped member with respect to the extending member adjusts the adjustable length between the nare flange and the distal tip. In one example, the corkscrew shaped member includes one or more detents, such as spherical detents, that adjust the adjustable length in discrete increments. For example, the device may have an indicator portion that allows the user to select a particular length associated with a patient's height, using an accepted correlation of height to the operative nare to epiglottis distance, by rotating a first portion of the device relative to a second portion of the device. For example, the indicator portion may have a mark, arrow or window that points to or exposes a number, letter or other symbol that is associated with a particular range of patient height for the optimal length of the adjustable nasopharyngeal device. In one example, a package housing is coupled to the nasopharyngeal device such that rotating a portion of the package housing adjusts the length of the nasopharyngeal device, while the nasopharyngeal device is sealably retained within the package housing. In one example, a corkscrew is formed from a wire or spiral metal member that is retained on a spool by projections on the spool that extend and retrieve a portion of the wire corkscrew as the spool is rotated around the direction extension, along the length of the nasopharyngeal device. In another example, a push button adjustment mechanism allows the length to be adjusted by pushing a button without requiring the housing to be rotated.

For example, a nasopharyngeal device may comprise an adjustment mechanism comprising a bolster on a first portion; a tubular airway portion extending away from the bolster wherein a continuous airway is provided through an entire length of the airway defined through the bolster and the tubular airway portion; and the tubular airway portion extends from a proximal end adjustably coupled with the first portion of the adjustment mechanism to a distal tip of the tubular airway portion, wherein the first portion is adjustably coupled to the proximal end of the tubular airway portion such that the first portion slidingly adjusts a length of the first portion within the proximal end of the tubular airway portion such that a distance between the bolster and the distal tip is selectively adjusted to a specific nare to epiglottis distance. In one example, the adjustment mechanism rotatingly engages the first portion to the tubular airway portion such that rotating the first portion relative to the tubular airway portion slides the first portion within the tubular portion adjusting the distance between the bolster and the distal tip. For example, rotating the first portion in a first rotational direction shortens the distance between the bolster and the distal tip and rotating the first portion in a second rotational direction, opposite of the first rotational direction, lengthens the distance between the bolster and the distal tip. In one example, the first portion comprises ribs extending radially outward from a surface of the first portion, and the ribs matingly engage a corkscrew member, the corkscrew member may be fixedly engaged within the proximal end of the tubular airway portion such that when the first portion is rotated, the ribs engage the corkscrew member such that the first portion slides within the proximal end of the tubular airway portion adjusting the length between the bolster and the tip of the tubular airway portion. For example, tubular airway portion comprises a flexible biocompatible material, such as a silicone or a thermoplastic elastomer or a rubber. The distal tip may comprise a bevel or a rounded off tip. In one example, the bevel improves the insertability of the device. The first portion of the adjustment mechanism may be made of a different material than the biocompatible material of the tubular airway portion, such as selecting a material more rigid than the biocompatible material of the tubular airway portion, such as a polycarbonate or a polyethylene.

In one example, the first portion may comprise a corkscrew shaped portion for rotatingly selecting the distance between the bolster and the distal tip. The corkscrew shaped portion may comprise detents for selecting discrete changes in the distance between the bolster and the distal tip. The detents may be beads that click into respective cavities.

The device may be packaged such that the tubular airway portion is contained within sterile packaging while the adjustment mechanism is available for adjusting the distance between the bolster and the distal tip without removing the device from the sterile packaging. The packaging may be comprised of a rigid plastic material formed into a clam shell housing that clamps down and prevents rotation of a portion of the device, while a rotational device matingly engages the adjustment mechanism, adjusting the distance between the bolster and the distal tip by rotating the adjustment mechanism while the device remains within the sterile packaging. A stationary portion of the adjustment mechanism may comprise an indicator that aligns with a number, letter or other device that indicates a setting corresponding to the distance between the bolster and the distal tip. For example, a removable tool may be used, and the removable tool may engage a matingly configured portion of the adjustment mechanism such that the tool rotatingly engages the adjustment mechanism such that the distance between the bolster and the distal tip is adjusted by rotating the tool.

Alternatively, a push button mechanism may allow adjustment of the length, and a window in the push button mechanism may indicate the adjusted length of the tube when utilizing the push button to adjust the length to the distal tip of the tubular airway portion. In this example, the distal tip may comprise a plurality of fenestrations or holes through the distal tip allowing air flow through any or all of the holes. For example, one or more of the holes may be used to engage protrusions from a housing that forms a distal portion of the case, which may be used to adjust the distance to the distal tip of the tubular airway portion when the holes of the tubular airway portion are engaged by the protrusions from the housing of the lower case, during adjustment of the length using the push button mechanism, and for protecting the tubular airway portion prior to use of the tubular airway portion. For example, the push button mechanism may be integrally formed as a portion of a proximal portion of the case, such as by polymer die injection of the proximal portion of the case with an integrally formed push button mechanism. A window may be integrally formed as a portion of the push button mechanism, the window being disposed over indicators integrally formed or adhered to an outer surface of the housing that forms the distal portion of the case. Thus, when the button of the push button mechanism is pushed, the user may observe the indicator numbers, letters or the like that are displayed in the window and may slide the portion of the case with the push button mechanism in relation to the housing of the lower case in order to adjust the distance of the holes of the distal tip of the tubular airway portion that is engaged by the protrusions from housing that forms the distal portion of the case. For example, this push button mechanism quickly adjusts the length of the adjustable tubular airway portion for a particular patient without removing the adjustable tubular airway portion from its protective packaging, until the length of the tubular airway portion is selecting and the tubular airway portion of the device is removed from the packaging immediately prior to insertion of the tubular airway portion into the patient's airway. The tip of the tubular airway portion may be open or closed, rounded or beveled.

With respect to the example of a beveled tip, an inside portion of the distal tip may comprise a first triangular face whereby the first triangular face deflects the distal tip when the distal tip is inserted and engages a posterior pharynx of a patient. Also, the inside portion of the distal tip may comprise a second face, adjacent to the first triangular face, and the second face directs devices inserted through a central lumen of the tubular airway portion upward, whereby the devices are directed away from an epiglottis of a patient.

BRIEF DESCRIPTION OF THE DRAWINGS

The following drawings are illustrative examples and do not further limit any claims that may eventually issue.

FIG. 1 illustrates an example of an adjustable nasopharyngeal device.

FIG. 2 illustrates a detailed view of an example of a corkscrew shaped member.

FIG. 3 illustrates a detailed view of another example of a corkscrew shaped member.

FIG. 4 illustrates another view of a corkscrew shaped member.

FIG. 5 illustrates an example of a package housing.

FIG. 6 illustrates an example of a selector for selecting a length setting.

FIG. 7 illustrates another view of a package housing.

When the same reference characters are used, these labels refer to similar parts in the examples illustrated in the drawings.

DETAILED DESCRIPTION

Figures 8, 9:
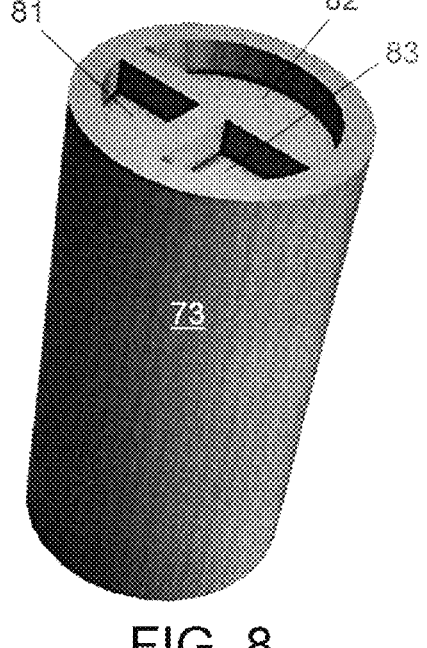
FIG. 8 illustrates another example of a selector.
FIG. 9 illustrates an alternative example of a distal tip.

In one example, as illustrated in FIG. 1, an adjustable nasopharyngeal device 10 is capable of adjusting the nare to epiglottis distance.

Herein, the nare to epiglottis distance means the distance from a bolster/flange 11, which is positioned adjacent to the external nare surface of a patient, to the distal tip of the device 12, which pushes the tongue. For example, a first portion 13 of the device may be matingly engaged with a second portion 14 of the device, rotatably, such that rotating the first portion relative to the second portion shortens the nare to epiglottis distance when rotating in a first rotational direction and lengthens the nare to epiglottis distance when rotating in a second rotational direction, opposite the first rotational direction. The first portion is referred to as the proximal end of the device and the second portion is referred to as the distal end of the device. For example, the proximal end may include a tubular airway made of a flexible biocompatible material such as a thermoplastic elastomer, silicone, rubber or the like. The distal end may include a tubular airway in fluid communication with the tubular airway of the proximal end and may be made of the same material or different materials as the proximal end. For example, a distal tip 12 may comprise a bevel to allow for easier insertion and fewer complications and/or abrasions when inserted. Alternatively, the distal tip may be rounded over to reduce complications and not beveled. In one example, the proximal end, or a portion thereof, is made of a more rigid material, having a harder durometer, than the distal end, such as a polycarbonate, polyethylene or the like. In one example, the proximal end adjustably slides into the distal end for increasing or decreasing the nare to epiglottis length.

In an example illustrated in FIG. 2, a detailed view of an internal corkscrew shaped portion 20 is shown in relation to a rotatable flange 22. For example, slots 21 may serve as detents for selecting discrete lengths during rotation of the corkscrew shaped portion 20. Alternatively, as illustrated in the partial cutaway detail view of FIG. 3, the proximal end may include a corkscrew shaped portion 35 rotationally inserted into a matingly channeled portion of the distal end, or an intermediate portion disposed between the proximal end and the distal end. In this example, detents are provided by bulbous spheroidal beads 37 that matingly fit into cavities 36 such that the beads 37 click into the cavities 36 providing discrete increases and decreases in the nare to epiglottis length. For clarity, the left side of FIG. 3 shows the raised corkscrew shape 39 connecting the beads 37 on an outer surface of the corkscrew shaped portion 35. The right hand side shows a cross section of 35 showing the wall defining the airway fluidically coupling the proximal end and distal end of the device.

In one example, the device is packaged such that the length of the device may be adjusted without removing the device from the packaging. Thus, the packaging is part of the device and is not merely for protecting the device from contamination and mechanical damage. For example, FIGS. 5 and 7 illustrate an example of the sealed packaging with a top half 71 and a bottom half 72 matingly configured for sealing to the top half 71. At a proximal end 73 of the packaging a sealed fitting may be rotatingly fitted within the packaging to allow adjustment of a portion of the device, such as the proximal end of the device, which may be engaged rotatingly with the fitting in the pro. The packaging may be of a rigid plastic, such as a polycarbonate, polyethylene or the like. The clam shell housing may clamp down on the device and prevent its movement and/or rotation of the device, while a rotational device sealingly mates with a portion of the device that rotational lengthens or shortens the device within the package. For example, FIG. 6 illustrates an adjustment device that extends from the packaging and matingly engages with the proximal end of the packaging and the rotational mechanism of the device. The adjustment device may lengthen or shorten the device by rotating a top knob 61 that is connected to a rotational member 64 that extends into an NPA within the package to engagingly couple the corkscrew shaped portion 35 of the device. The knob 61 is sealingly coupled, rotationally, with a stationary portion 66. The stationary portion may have an indicator 63 that aligns with a number, letter or other device 62, which indicates a setting that corresponds to a length of an adjustable nasopharyngeal device contained within the packaging. Thus, the length of the adjustable nasopharyngeal device may be adjusted within the package housing to one of a plurality of discreet length settings without removing the device from the packaging. This prevents contamination or any other damage to the adjustable nasopharyngeal device while the device is being set to the correct nare to epiglottis length for a particular patient, which may be based on an observable correlation, such as height of the patient.

In one example, a removable tool (or 'key') may be used to adjust the length of the device, whether in the package housing or after removal from the package housing. For example, FIG. 8 illustrates a detail for an example of proximal portion of a package housing that has indentations 81, 82, 83 that are matingly shaped for engaging a tool for adjusting the length of an adjustable nasopharyngeal device within the package.

An inside portion of the distal tip of a device may assist in placement of the device, for example. As illustrated schematically in FIG. 9, a first face B of the triangle deflects the distal tip from the posterior pharynx for example, which directs the tip downward towards the epiglottis. A second face A helps to direct other devices inserted through the lumen at the distal tip upward and away from the epiglottis. The third face C reinforces the anterior portion of the distal tip preventing fold-over of the bevel during insertion.

Figure 10:
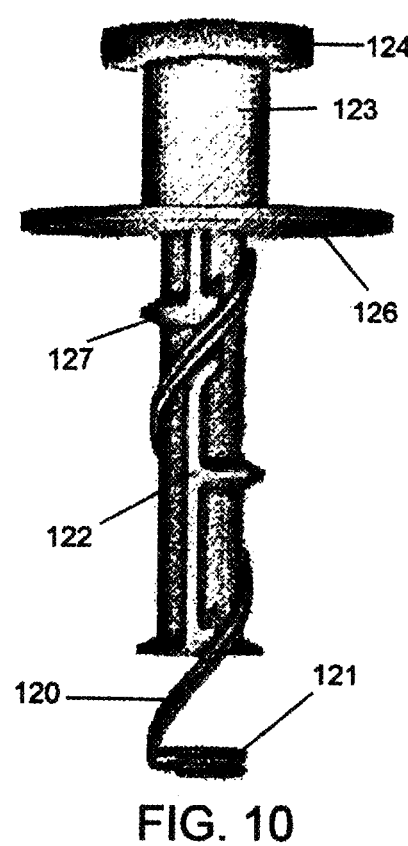
FIG. 10 illustrates another example of a corkscrew shaped member.
Figure 11:
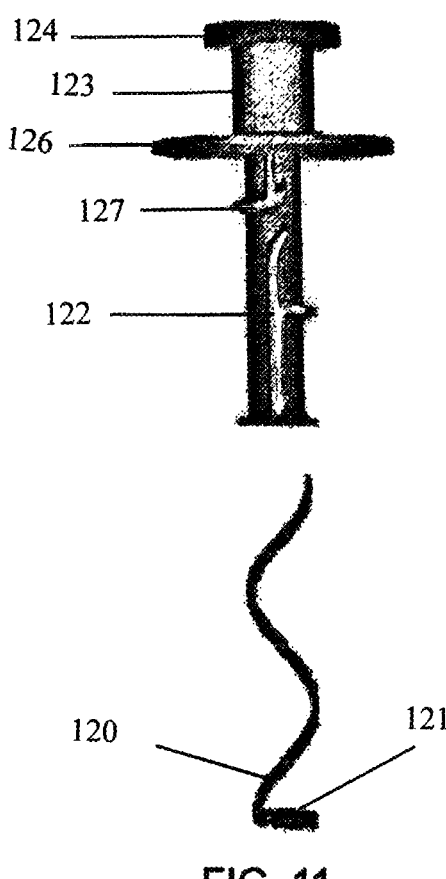
FIG. 11 illustrates an exploded view of the corkscrew shaped member of FIG. 10.

In one example, a raised corkscrew shape is provided using a corkscrew adjustment member, as illustrated in the exploded view of FIG. 11, for example. The corkscrew adjustment member 120 may be made of a metal, such as spring steel. The material of the corkscrew adjustment member is rigid enough to keep its shape while being flexible enough to operatively adjust the length of the adjustable nasopharyngeal device. FIG. 10 shows how the corkscrew adjustment member 120 is engaged into channels on a shaft extending from a flange 116 and may be defined by raised ribs 122, 127 protruding from the shaft of a corkscrew adjustment extending handle 123. A coupling member 124 on the handle 123 is provided for engaging with a key or rotating knob device that may couplingly rotate the handle 123. The loop 121 of the corkscrew adjustment member engages the distal portion of the device such that the distal end extends and retracts as the handle rotates.

Figure 12:
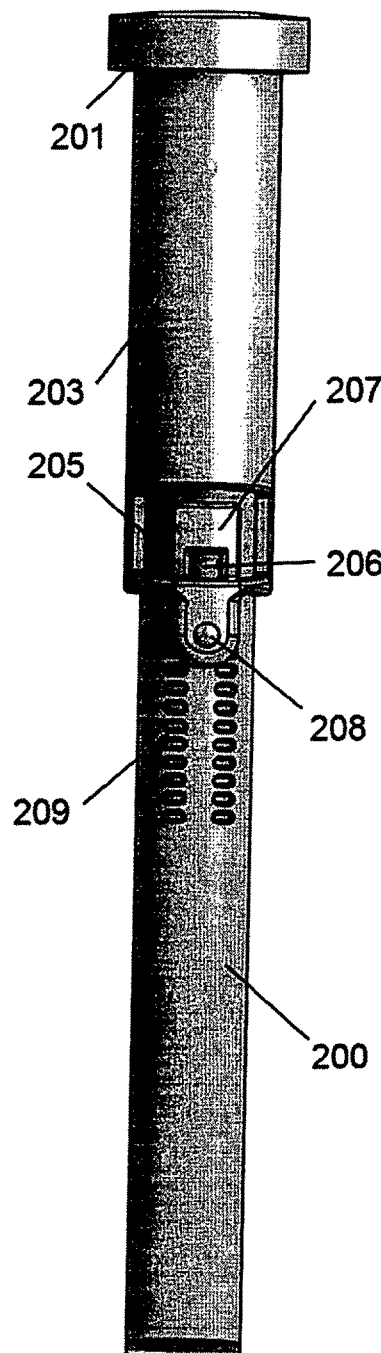
FIG. 12 illustrates an alternative example of an adjustment mechanism for an adjustable nasopharyngeal device.

In an alternative example, as illustrated in FIG. 12, a push button mechanism 207 is provided for adjusting a nare to epiglottis distance of an adjustable nasopharyngeal device contained within a protective case. For example, a window 206 in the push button mechanism 207 provides an indication of the nare to epiglottis distance of an adjustable tubular airway device, when utilizing a push button 208 of the push button mechanism 207 to adjust the nare to epiglottis distance of a tubular airway contained within the case 203 of the example illustrated in FIG. 12. A bolster flange cover 201 encloses a flange 301 of the bolster, flange 301 being best seen in FIG. 14, for example, and the flange cover 201 is defined as the proximal end of the case since it covers the proximal end of the tubular airway.

A push button mechanism 207 may be integrally formed, such as by polymer die injection molding, together with the case 203 illustrated in FIG. 12. For example, the push button mechanism 207 may be coupled to an upper housing of the case 203 by thin coupling members, which are defined by a U-shaped absence of polymer material 205, defining both the thin coupling members of the push button mechanism 207 and the remainder of the push button mechanism 207 including the push button 208 and an indicator window 206 for displaying writing disposed on the surface of a distal end of the case engaged within the proximal end of the case. For example, the distal end of the case 200 may be slidingly extended or retracted within the proximal end of the case by depressing the push button 208, and when the push button 208 is released, protrusions from a portion of the push button mechanism 207 engages slots 209 in the surface of the distal end of the case 200, preventing further movement of the distal end of the case 200 relative to the proximal end of the case 203.

Figure 16:
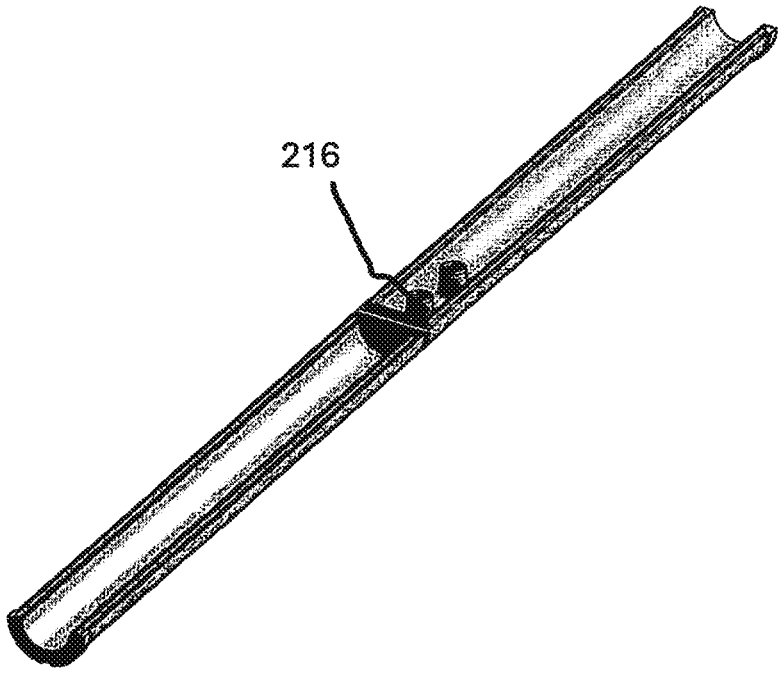
FIG. 16 illustrates an example of an external housing in a pre-assembled view.
Figure 17:
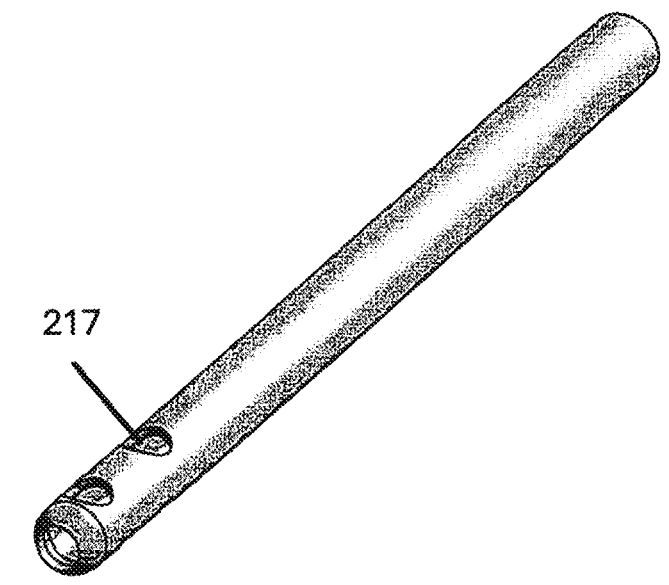
FIG. 17 illustrates an example of a distal portion of a tube in a pre-assembled view.

In this alternative example, the distal tip may comprise a plurality of fenestrations or through holes 217 that pass through the wall forming the distal tip, allowing air to flow through any or all of the holes 217, along a central tubular continuous airway, and extending through the bolster at the proximal end of the continuous airway, as illustrated in FIG. 17, for example. These holes 217 may be engaged by protrusions 216 from the housing that forms a distal portion of the case, as illustrated in FIG. 16, for example, which is used to adjust the distance to the distal tip of the tubular airway portion with respect to the bolster at the proximal end of the tubular airway. For example, the holes 217 of the tubular airway portion may be engaged by the protrusions 216 from the housing, and the nare to epiglottis distance is adjusted by sliding the housing that forms the distal portion of the case 200 relative to the proximal portion of the case by depressing the push button 208 of the push button mechanism 207, which may be integrally formed as a portion of the proximal portion of the case 203, such as by polymer die injection of the case 203. The case may be cast in two halves that are joined together to form the proximal portion of the case 203, the front half being illustrated in FIG. 19, for example, and two halves that form the distal portion of the case 200, both halves being illustrated in FIG. 16, for example. The case both protects the tubular airway portion prior to use with a patient and provides a length adjustment mechanism for accurately adjusting the nare to epiglottis distance.

For example, the push button mechanism may be integrally formed as a portion of a proximal portion of the case, such as by polymer die injection of the proximal portion of the case with an integrally formed push button mechanism. A window 206 may be integrally formed as a portion of the push button mechanism, as illustrated in FIG. 12, the window being disposed over indicators integrally formed on or adhered onto an outer surface of the housing that forms the distal portion of the case, such that numbers, letters or other indicators are viewable through the window to easily select the correct nare to epiglottis distance. Thus, when the button of the push button mechanism is pushed, the user may observe the indicator numbers, letters or the like that are displayed in the window and may slide the portion of the case with the push button mechanism in relation to the housing of the lower case in order to adjust the nare to epiglottis distance. Thus, the holes of the distal tip of the tubular airway portion may be positioned properly for each patient prior to insertion of the device into the patient's airway.

Protrusions 216 extend from an inner surface of the housing that forms the distal portion of the case, as illustrated in FIG. 16, for example. These protrusions 216 are sized and positioned for engaging corresponding holes 217 in the adjustable tubular airway portion illustrated in FIG. 17, for example. Thus, extension or retraction of the housing using the push button mechanism extends and retracts the nare to epiglottis distance, quickly adjusting the length of the adjustable tubular airway portion for a particular patient without removing the adjustable tubular airway portion from its protective packaging, until the length of the tubular airway portion is selected and the tubular airway portion of the device is removed from the packaging, prior to insertion of the tubular airway portion into a particular patient's airway. For example, the window may show a height in feet and inches, and the nare to epiglottis distance may be selected by positioning the window of the push button mechanism over the height in feet and inches of the patient.

Figure 14:
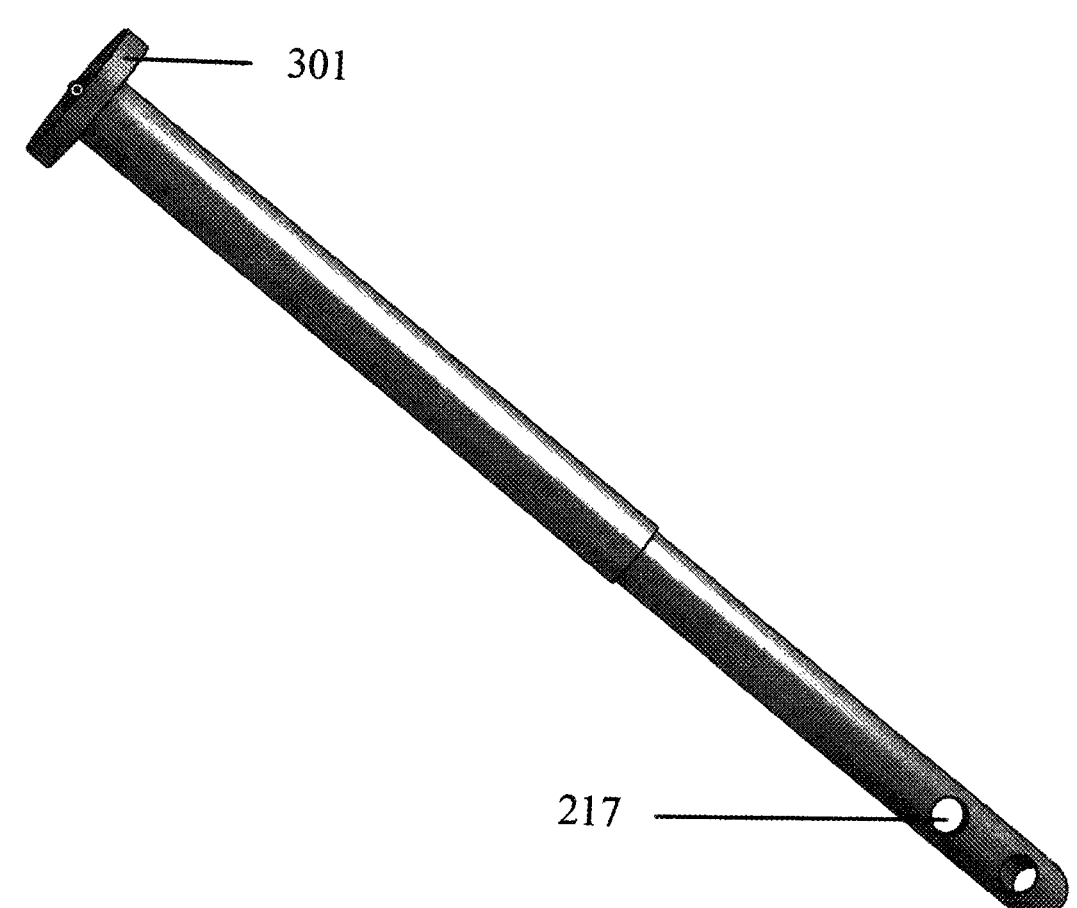
FIG. 14 illustrates a perspective view of an example of a tubular airway portion of an adjustable nasopharyngeal device, the tubular airway portion being made of a flexible biocompatible material and being set to a particular nare to epiglottis distance as inserted into a patient.
Figure 18:
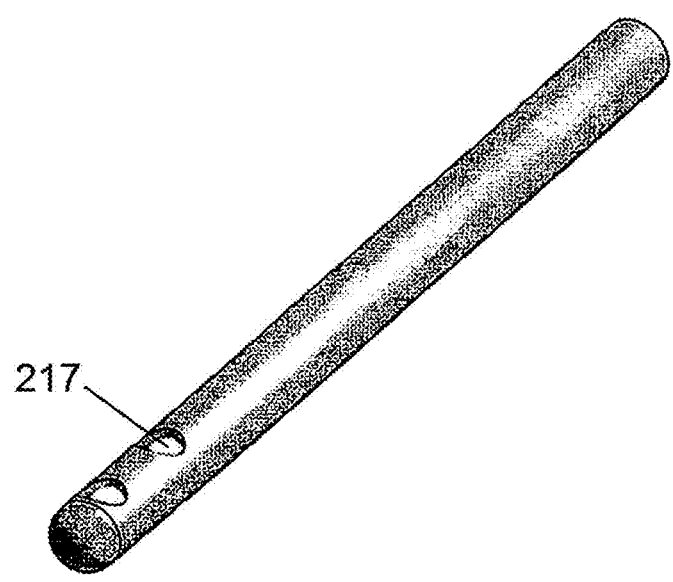
FIG. 18 illustrates another example of a distal portion of a tube in a pre-assembled view.

For example, the distal tip of the tubular airway portion may be open or closed, rounded or beveled. As illustrated in FIG. 17, the distal tip may be open and rounded. Alternatively, as illustrated in FIG. 18, the distal tip may be closed and rounded, for example. FIG. 14 illustrates a perspective view of an example of a tubular airway portion of an adjustable nasopharyngeal device, the tubular airway portion being made of a flexible biocompatible material and being set to a particular nare to epiglottis distance as inserted into a patient. A bolster is illustrated on the proximal end and a closed and rounded tip of the example illustrated in FIG. 18 is illustrated at the distal end.

Figure 13:
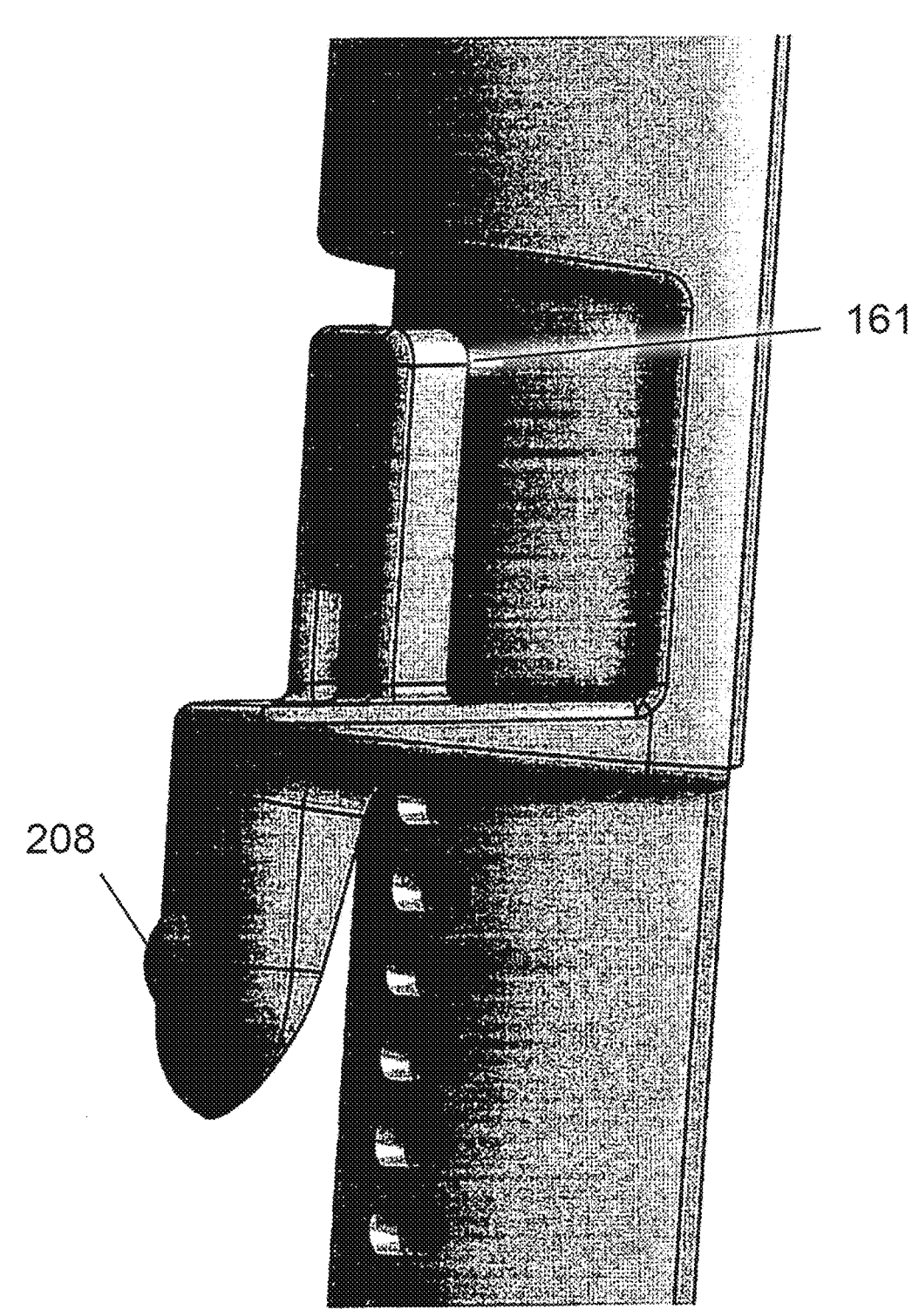
FIG. 13 illustrates a detailed, perspective view of a push button adjustable locking mechanism of the alternative example of FIG. 12.
Figure 15A:
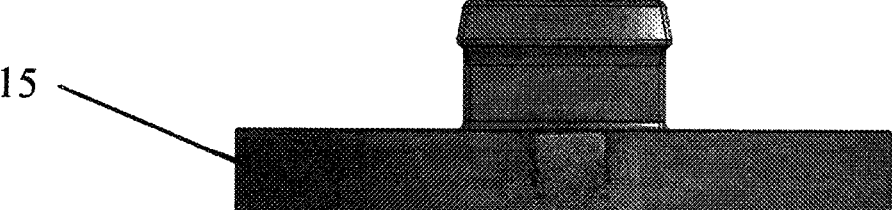
FIG. 15A illustrates a side view of a C-shaped locking member.
Figure 15B:
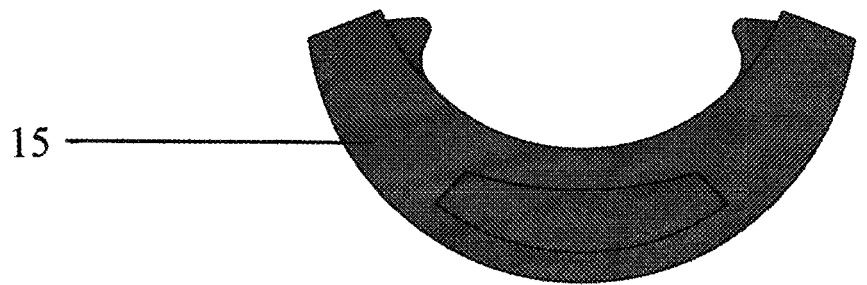
FIG. 15B illustrates a top view of the C-shaped locking member of FIG. 15A.
Figure 15C:
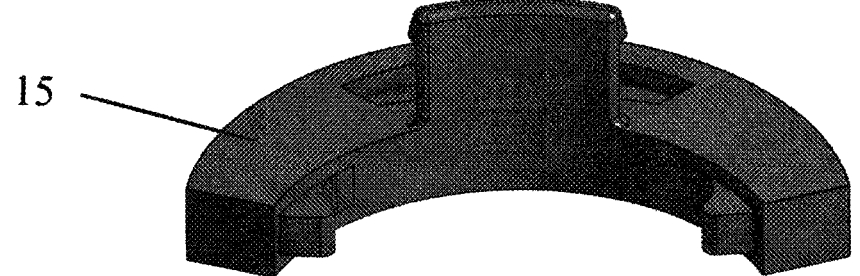
FIG. 15C illustrates a perspective view of the C-shaped locking member of FIGS. 15A and 15B.
Figure 19A:
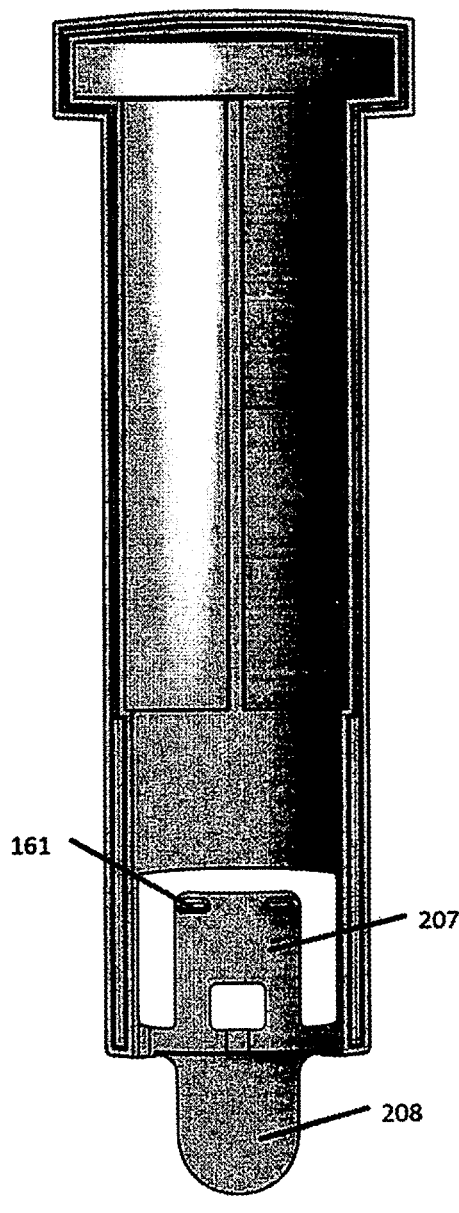
FIGS. 19A-19C illustrate views of two halves of the proximal portion of the case illustrated in FIG. 12 that are not shown in FIG. 12, providing detailed views of (A) the interior of the front half, (B) the exterior back half with the C-shaped locking member shown, and (C) the interior back half, opposite of the exterior back half, with the C-shaped locking member shown.
Figure 19B:
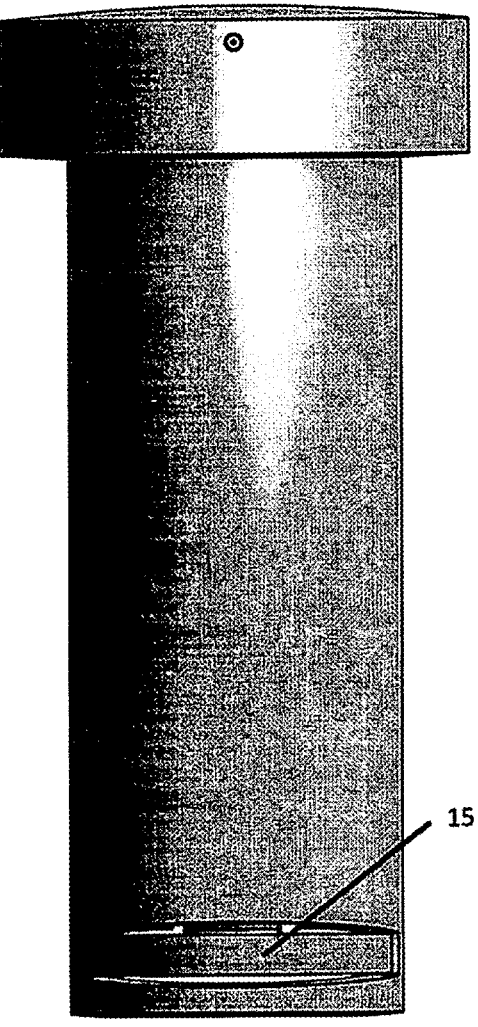
Figure 19C:
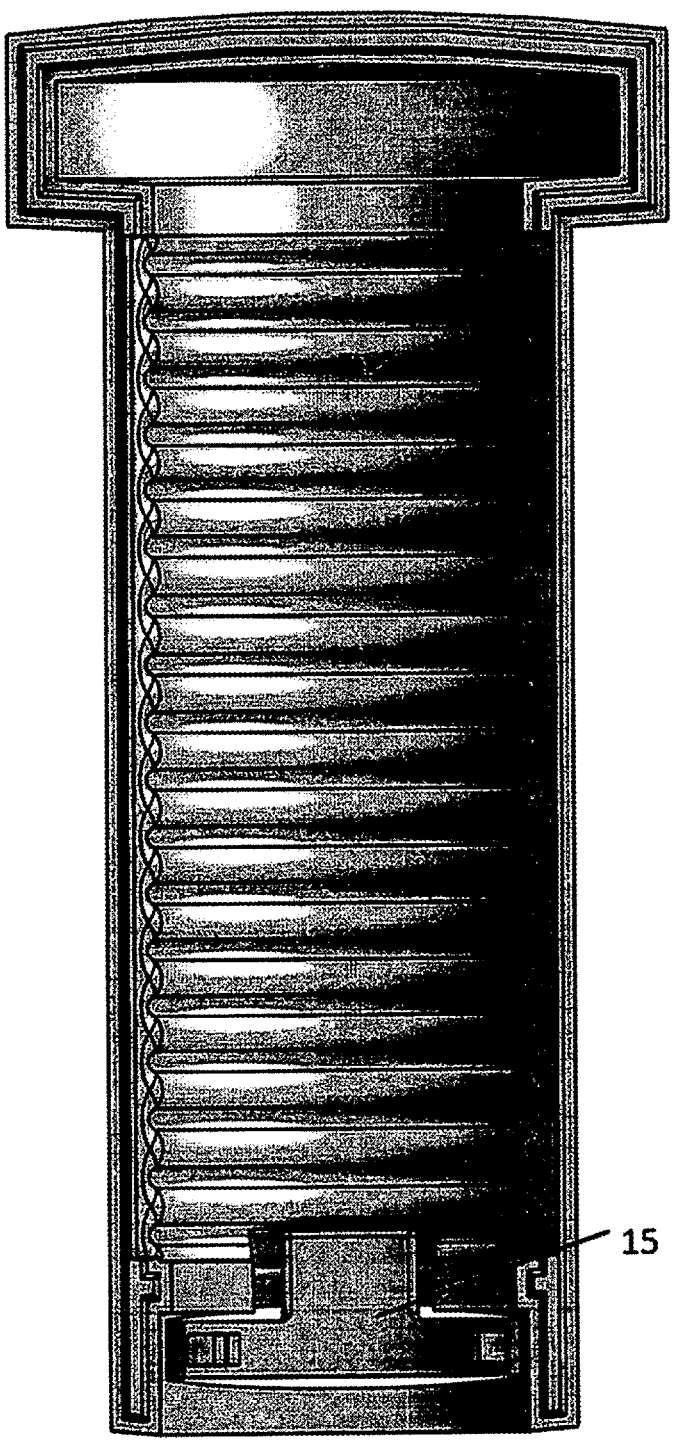
Figure 20:
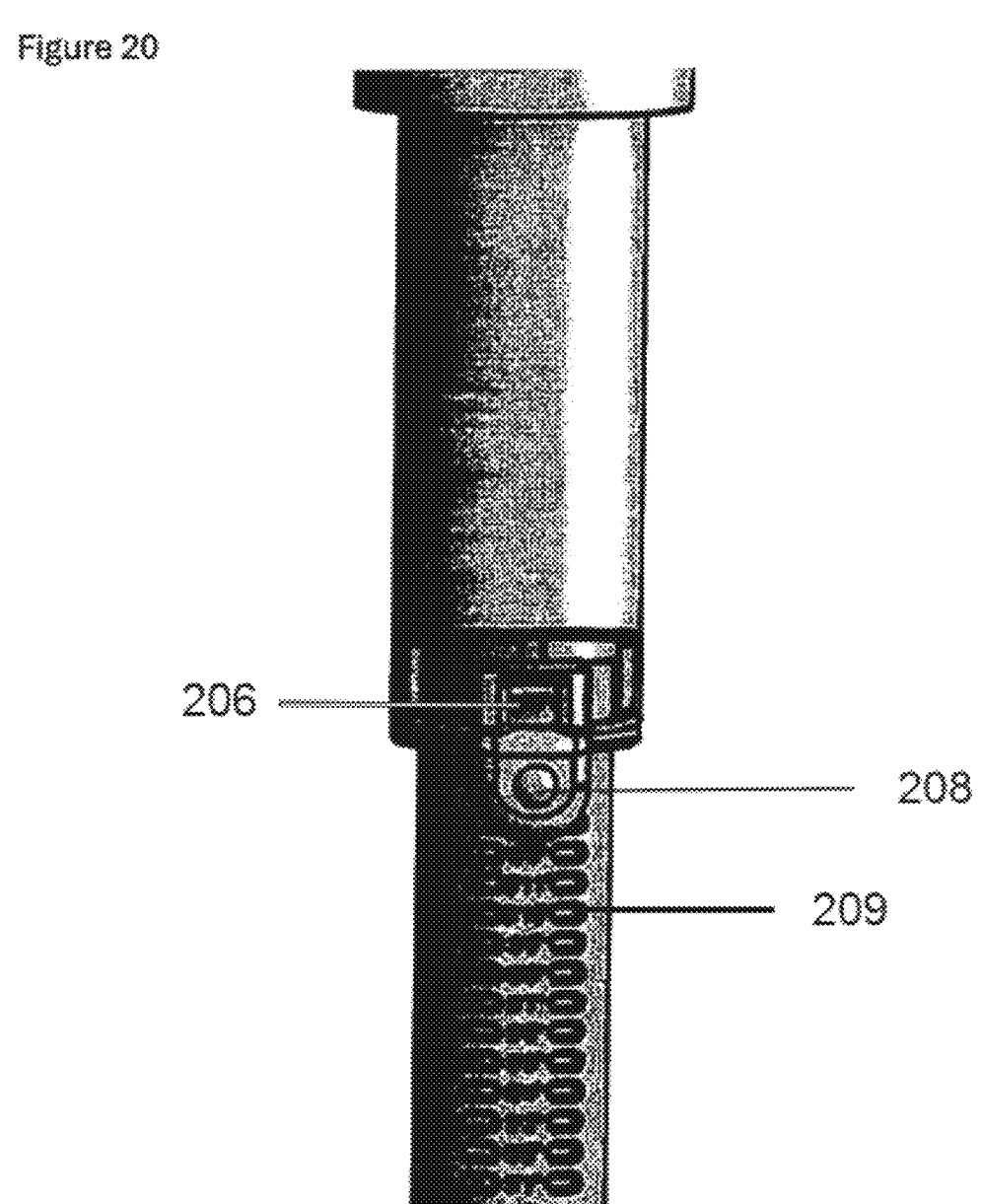
FIG. 20 illustrates an example of a use of indicators that are formed on a surface of the housing and are displayed within a window of the push button mechanism.

FIG. 15A illustrates a detailed side view of a C-shaped locking member 15, which locks the housing of the distal end of the case into the proximal end of the case. FIG. 15B illustrates a top, detailed view of the C-shaped locking member of FIG. 15A. FIG. 15C illustrates a perspective, detailed view of the C-shaped locking member of FIGS. 15A and 15B. FIGS. 19A-19C illustrate views of two halves of the proximal portion of the case illustrated in FIG. 12. These views provide details not shown in FIG. 12, including the mating portions of the housing halves that may be used to join opposite halves of polymer die cast portions of the housings. FIG. 19A illustrates an interior of the front half of a proximal portion of the case, providing a detailed view of the protrusions 161 of the push button mechanism. The detailed view of FIG. 13 shows how those same protrusions engage with the distal portion of the case and provide for quickly changing the nare to epiglottis distance. The views in FIGS. 19A, 19B and 19C show an example of the opposite halves of the proximal portion of the case that are not visible in FIG. 12. The exterior back half is shown in FIG. 19B with a portion of the C-shaped locking member visible. In FIG. 19C, an example of the interior back half, opposite of the exterior back half, shows the opposite side of the C-shaped locking member 15 and how it engages the interior of the back half of the proximal portion of the case. FIG. 20 shows a detailed view of an example of indicators viewable through the window of the push button mechanism. In one example, different indicators may be provided on opposite sides of the distal portion of the case, and the user may select the type of indicator desired merely by rotating the distal portion of the case. For example, by rotating the distal portion of the case 180 degrees relative to the upper portion of the case, the user may switch between a first indicator, such as height in feet and inches, and an alternative indicator, such as a nare to epiglottis distance indicator. Thus, the user may select the best indicator for the situation or may preselect a particular indicator based on operational training and preferences.

For example, FIG. 16 illustrates how the distal portion of the case may be formed in two halves of a housing in a clam shell configuration, such as by die injection molding. The clam shell housing is shown in a pre-assembled view and shows two protrusions 216, which may be inserted into holes 217 in the distal tip. This mechanism firmly engages the distal tip within the clam shell housing, and when the distal portion of the case is displaced in relation to the proximal portion of the case, the distal tip of tubular airway is extended or retracted in relation to the proximal portion of the tubular airway. Thus, setting the nare to epiglottis distance of the tubular airway portion of the device is greatly simplified and dangerous errors are reduced compared to methods requiring the user to select a device of the correct length in an emergency situation or having to use adjust a tube by manually shortening a tube based on measurements or the like.

FIGS. 17 and 18 illustrate two alternatives of the distal portion of a tubular airway portion of the device, shown prior to assembly. In FIG. 17, the end of the airway is open providing for the flow of air through the open end or through the holes 217 in the sides of the tubular airway portion. As an alternative example, the end of the airway in FIG. 18 is closed. However, the same holes as illustrated in FIG. 17 provide a continuous channel for air flow through the tubular airway portion of the device, nevertheless, providing air to the patient through the holes in the side walls of the tubular airway portion in FIG. 18.

This detailed description provides examples including features and elements of the claims for the purpose of enabling a person having ordinary skill in the art to make and use the inventions recited in the claims. However, these examples are not intended to limit the scope of the claims directly. Instead, the examples provide features and elements of the claims that, having been disclosed in these descriptions, claims and drawings, may be altered and combined in ways that are known in the art.

What is claimed is:

1. A nasopharyngeal device comprises:

an adjustment mechanism comprising a bolster on a first portion having a bolster flange extending radially outward from a bolster tube, and a removable case comprising a bolster flange cover, the bolster flange cover enclosing the flange of the bolster, wherein the bolster flange is a proximal end of the nasopharyngeal device;

a tubular airway portion defining a second portion of the nasopharyngeal device, the second portion extending away from the bolster and elongationally extendably coupling the first portion of the nasopharyngeal device;

wherein a continuous airway is provided through an entire length of an airway defined through the bolster tube of the first portion and the tubular airway portion of the second portion; and the tubular airway portion of the second portion extends from the proximal end and comprises a distal tip of the tubular airway opposite of the proximal end of the nasopharyngeal device, and the removable case further comprises a tubular housing encasing the second portion of the nasopharyngeal device, and the tubular housing of the removable case is adjustably coupled with the bolster flange cover of the removable case such that the tubular housing is elongationally extendably coupled to the bolster flange cover, such that elongationally extendably adjusting the tubular housing with respect to the bolster flange cover of the removable case slidingly adjusts a length of the first portion within the proximal end of the tubular airway portion such that a distance between the bolster flange of the first portion and the distal tip of the second portion is selectively adjusted to a specific nare to epiglottis distance.

2. The device of claim 1, wherein the bolster flange cover of the adjustment mechanism rotatingly engages the tubular housing of the adjustment mechanism such that the adjustment mechanism elongates the distance between the bolster flange of the first portion and the distal tip of the second portion when at least a portion of the bolster flange cover is rotated with respect to the tubular housing of the removable case, before the removable case is removed from the nasopharyngeal device prior to insertion of the nasopharyngeal device into a patient.

3. The device of claim 2, wherein rotating the at least a portion of the bolster flange cover in a first rotational direction shortens the distance between the bolster and the distal tip and rotating the at least a portion of the bolster flange cover in a second rotational direction, opposite of the first rotational direction, lengthens the distance between the bolster and the distal tip.

4. The device of claim 1, wherein the tubular airway portion comprises a flexible biocompatible material.

5. The device of claim 4, wherein the biocompatible material is of a silicone.

6. The device of claim 4, wherein the biocompatible material is of a thermoplastic elastomer.

7. The device of claim 4, wherein the distal tip comprises a bevel.

8. The device of claim 7, wherein an inside portion of the distal tip comprises a first triangular face whereby the first triangular face deflects the distal tip when the distal tip is inserted and engages a posterior pharynx of a patient.

9. The device of claim 8, wherein the inside portion of the distal tip comprises a second face, adjacent to the first triangular face, and the second face directs devices inserted through a central lumen of the tubular airway portion upward, whereby the devices are directed away from an epiglottis of a patient.

10. The device of claim 4, wherein the removable case is made of a different material than the biocompatible material of the tubular airway portion, and the removable case is removed prior to inserting the nasopharyngeal device into a patient.

11. The device of claim 10, wherein the different material is selected to be a material more rigid than the biocompatible material of the tubular airway portion.

12. The device of claim 11, wherein the different material is of a polycarbonate.

13. The device of claim 1, wherein the removable case is sterile packaging and protects the nasopharyngeal device from contamination while adjusting the specific nare to epiglottis distance of the nasopharyngeal device prior to inserting the nasopharyngeal device in the patient.

14. The device of claim 13, wherein the tubular housing is of a rigid plastic material formed into a clam shell housing that clamps down and prevents rotational and elongational movement of the second portion of the nasopharyngeal device with respect to the tubular housing of the removable case.

15. The device of claim 1, wherein the bolster cover comprises an indicator that aligns with a number, letter or other device on the tubular housing such that the indicator indicates a setting corresponding to the distance between the bolster flange and the distal tip.

\* \* \* \* \*